(12) United States Patent  (10) Patent No.: US 8,343,231 B1
Christoudias  (45) Date of Patent: Jan. 1, 2013

(54) SURGICAL MESH FOR HERNIA REPAIR

(76) Inventor: George C. Christoudias, Teaneck, NJ (US)

( * ) Notice: Subject to any disclaimer, the term of this patent is extended or adjusted under 35 U.S.C. 154(b) by 674 days.

(21) Appl. No.: 11/736,383

(22) Filed: Apr. 17, 2007

(51) Int. Cl.
*A61F 2/02* (2006.01)
(52) U.S. Cl. .................................................. 623/23.72
(58) Field of Classification Search ............... 623/23.72
See application file for complete search history.

(56) References Cited

U.S. PATENT DOCUMENTS 5,456,720 A * 10/1995 Schultz et al. ............ 623/23.64
6,596,002 B2 * 7/2003 Therin et al. ................. 606/151
2004/0087980 A1 * 5/2004 Ford et al. ..................... 606/151
2005/0043818 A1 * 2/2005 Bellon Caneiro et al. . 623/23.72

* cited by examiner

*Primary Examiner* — Melanie Tyson
*Assistant Examiner* — Son Dang
(74) *Attorney, Agent, or Firm* — David M. Quinlan, P.C.

(57) ABSTRACT

A surgical mesh for repair of incisional and or ventral hernia with a fixation fin extending from one of the surfaces of the mesh usually along the midline of the surface. The closure of the hernia defect edges involves suturing to the fin to avoid the possibility of damage to internal organs during laparoscopic suturing. An alternate embodiment involves a flexible rod mounted in a tubular structure on the mesh axis. The tubular structure includes a central opening with an attached thread that permits removal of the flexible rod, which spreads the mesh open to facilitate fixation of the mesh onto the abdominal wall surface.

17 Claims, 7 Drawing Sheets

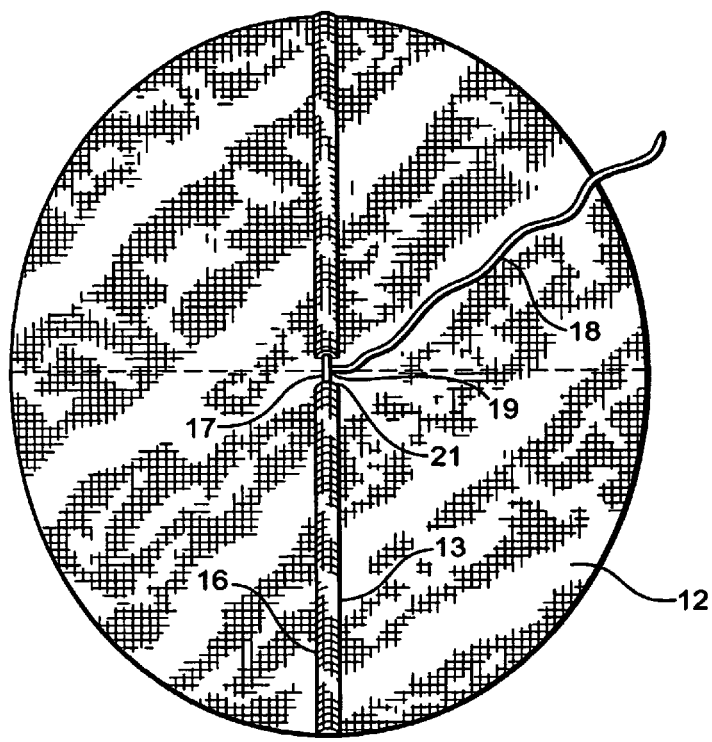
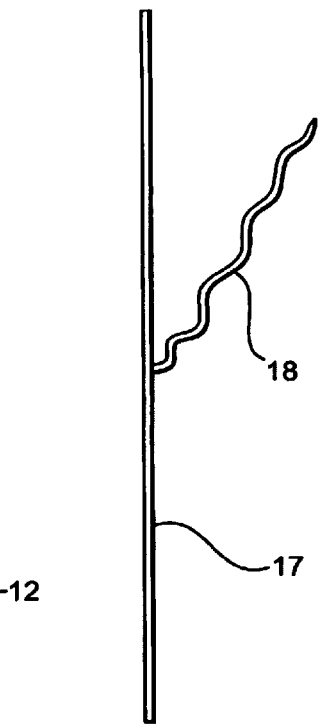
FIG. 2  FIG. 2C
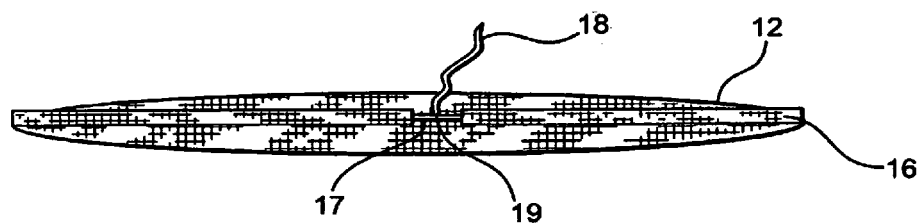
FIG. 2A
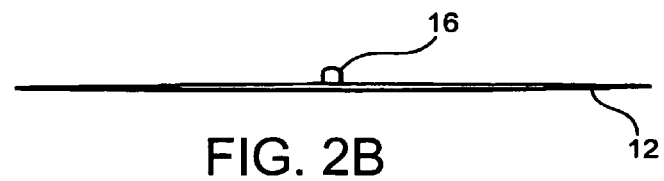
FIG. 2B

SURGICAL MESH FOR HERNIA REPAIR

The present invention comprises an improved surgical mesh for hernia repair having a fixation fin made of absorbable or non-absorbable surgical material or a combination of both.

In the current art of surgical repair of an incisional or ventral hernia (photograph 1a), a mesh is implanted to reinforce the repair and prevent reoccurrence of the hernia. In the laparoscopic method of hernia repair used by the inventor, the entrance to the peritoneal cavity is gained through an incision through the abdominal wall defect. A port is then inserted through the defect into the abdominal cavity and connected to a $CO_2$ source. A pneumoperitoneum is then established. A laparoscope is then entered into the abdomen through the port. Under video control, three more ports are introduced at three different points away from the hernia defect. The pneumoperitoneum is then evacuated and the port going through the defect is removed.

A surgical mesh of an appropriate size for the size of the defect (photograph 1b) is then inserted through the incision that was made first, over the defect, into the abdominal cavity (photograph 1c). The mesh is then sutured onto the edges of the hernia defect, if the defect is too large to be closed by approximation of the edges of the defect. If the edges of the defect can be approximated primarily by suture, then the mesh is incorporated in the repair. There is excess mesh of at least 4 cm, extending beyond the fixation line (photograph 1d). This excess mesh is then fixed onto the peritoneal surface of the abdominal wall (photographs 2b, 2c and 2d), after laparoscopically closure of the incision and reestablishment of the pneumoperitoneum. The excess mesh is seen suspended from the suture line (photograph 1d). The mesh is then spread smoothly onto the abdominal wall with a manipulating instrument and fixed in place with a stapling fixation device (photographs 2a, 2b, 2c and 2d).

Some potential problems can arise with this method. The following problems are related to the suturing of the mesh to the abdominal wall defect:

a) Surgery to the Underlying Intestine and/or Organ.

The intestines and/or organs are resting on the posterior surface of the mesh. The suture fixing the mesh on the defect has to enter through the anterior to posterior surface of the mesh and then through the posterior to the anterior surface of the mesh. The potential for the suture to go through the intestine/organ resting on the posterior surface of the mesh while suturing the mesh is real and can lead to severe consequences resulting from the injury to the intestine/organ.

b) Placing the Suture Through the Mesh.

If the excess portion of the mesh is lying by the suture site, it could be inadvertently caught by the suture and folded over on itself. This would impede the unfolding and fixation of the mesh onto the abdominal wall, making it necessary to remove the suture of the repair and start the repair all over again, causing unnecessary delays.

c) Wrinkling of the Mesh by the Suture.

If the suture is not placed in a perfectly straight line on the mesh engaged on the suture line, then wrinkling of the mesh will result. This renders the spreading and fixation of the mesh onto the abdominal wall problematic, compromising perfection.

The present invention comprises an improvement of the currently used surgical hernia repair mesh. The improved mesh will facilitate the fixation of the mesh on the edge of the hernia defect including a fixation fin, which is incorporated in the repair. This prevents injury to the underlying intestine or other abdominal organs. It further facilitates the spreading of mesh onto the abdominal wall surface in preparation for the fixation of said mesh in place with the appropriate fixation device with staples by providing a central stiff ridge, which extends alongside the midline of the mesh. The stiff ridge maintains the mesh expanded and facilitates spreading said mesh and fixing it onto the abdominal wall with the appropriate staples.

A second embodiment comprises an improved surgical mesh, which includes a tubular pocket along the long midline of the mesh with an opening in the center for removal of a flexible mesh spreader from the pocket. A suture or thread is attached to the flexible mesh at the opening of the pocket to facilitate removal of the flexible mesh spreader from the opening.

Accordingly, the object of this invention is to provide a new and improved surgical mesh for hernia repair.

Another object of this invention is to provide a new and improved surgical mesh for hernia repair including a fixation fin extending at a right angle therefrom to facilitate the fixation of the mesh on the edge of the hernia defect to prevent injury to the underlying intestine and other abdominal organs.

A further object of this invention is to provide a new and improved surgical mesh particularly for laparoscopic surgery which includes a fixation fin to facilitate the spreading of mesh onto the abdominal wall surface by providing a central stiff ridge which maintains the mesh expanded and facilitates spreading and fixing it onto the wall with staples while the fin is incorporated in the suturing repair.

The above and other objects and advantages of the present invention may be more clearly seen when viewed in conjunction with the accompanying drawings wherein:

FIG. 2 is a front view of an alternate embodiment of the invention including a tubular midline pocket;

FIG. 2A is a side perspective view of the mesh design shown in FIG. 2;

FIG. 2B is an end view of the mesh design shown in FIG. 2;

FIG. 2C is a view of the flexible rod and attached thread;

FIGS. 9A, 9B, 9C, and 9D comprise photographs 1a, 1b, 1c, and 1d, respectively, of the actual hernia.

FIGS. 10, 10B, 10C, and 10D comprise photographs 2a, 2a, 2c, and 2d, respectively, of the hernia repair.

Figure 1:
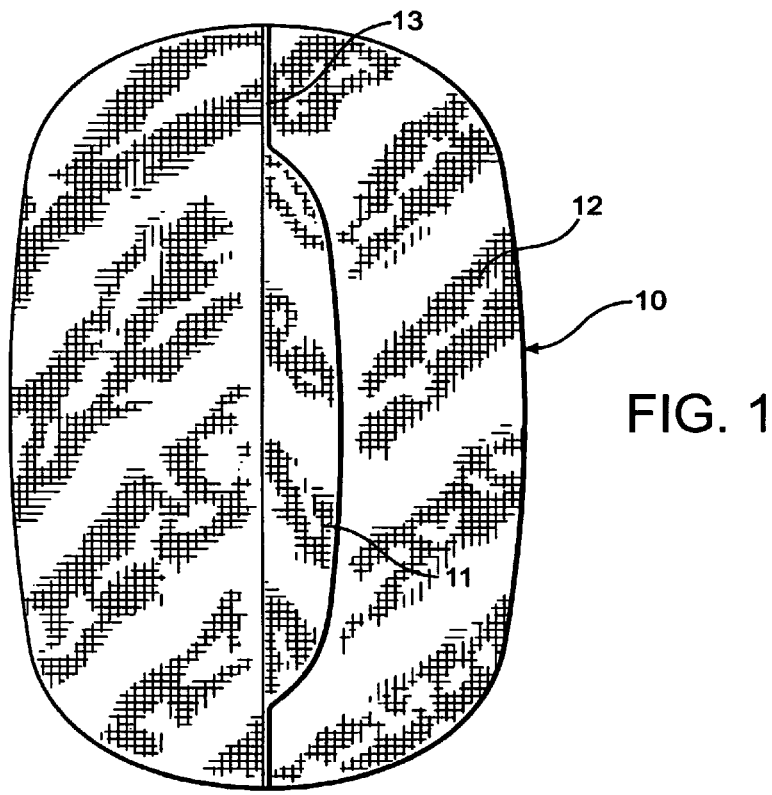
FIG. 1 is a front view of a surgical mesh with a fixation fin and stiff central ridge.
Figure 1A:
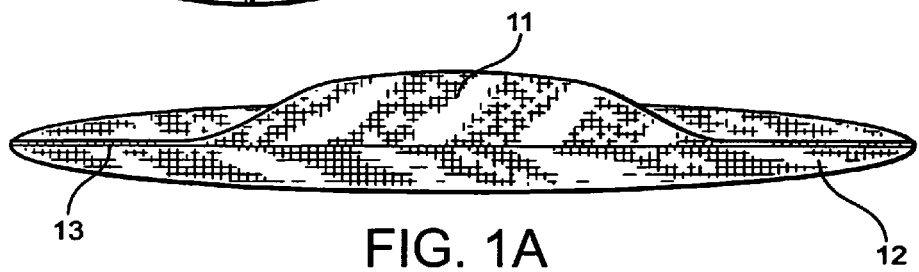
FIG. 1A is a side perspective view of the mesh design shown in FIG. 1.
Figure 1B:
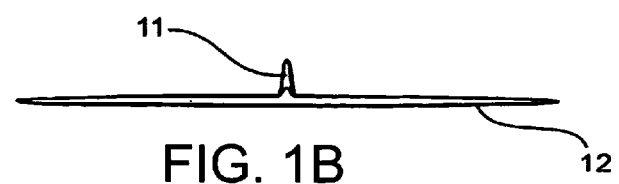
FIG. 1B is an end view of the mesh design shown in FIG. 1.

As shown in the drawings particularly FIGS. 1, 1A, and 1B, the invention comprises a surgical mesh 10 for hernia repair having a fixation fin 11 of absorbable or non-absorbable surgical material mounted thereon. The fin 11 extends at the right angle from one of the surfaces of the main hernia repair mesh 12 usually along the midline 13 of the surface. When the mesh 12 is placed into the abdomen 20, as described in the background of the invention, the fixation fin 11 is projecting in the direction leading away from the abdominal cavity. The mesh 12 can then be fixed onto the defect 14 by suturing the fixation fin 11 and avoiding suturing through the main body of the mesh 12. In this way no needle or suture penetrates the main body of the mesh 12 and this eliminates the danger of a) injury to the bowel layer resting on the posterior surface of the mesh 12; b) imaging and suturing an additional fold of the excess mesh which would impede opening, spreading and fixing the mesh 12; and c) wrinkling the mesh 12 and impeding the opening, spreading and fixing the mesh 12.

The present invention further comprises a flexible stiff ridge 15 alongside the midline 13 of the mesh 12, which will lift the mesh 12 alongside the abdominal wall 21 and facilitate the spreading on either side of the mesh 12 and its fixation onto the abdominal wall 21. Said flexible stiff ridge 15 may be made either of absorbable or non-absorbable surgical material and is incorporated alongside the midline of the main body of the mesh 12.

An alternate embodiment of this invention shown if FIGS. 2, 2a and 2b comprises a tubular elongated structure or pocket 16 extending alongside the midline 13 of the main body of the mesh 12 on one of its surfaces at the center of the mesh 12 allowing the insertion of a thin, removable, flexible rod 17, which, when inserted into the tubular structure 16 of the mesh 12, will maintain said mesh 12 in an expanded condition. Said rod 17 has a strong thread 18 affixed onto its center 19 and pull on this thread 18 will remove the rod 17 from the mesh tube 16.

Referring now to FIG. 1 of the drawings, the invention comprises an overview of a hernia repair mesh 10 with a main body of the mesh 12, a fixation fin 11 and a central stiff ridge 13. A side view along the axis of the mesh 12 and the short axis of the mesh 12 are also demonstrated.

An alternate embodiment is shown in FIG. 2 comprises a mesh 12 with a central tubular structure 16 with an opening 25 at the center. A flexible rod 17 with a thread 18 for removal of said rod 17, is inserted into said tubular structure 16 to maintain the mesh 12 in an expanded portion and facilitate its fixation onto the abdominal wall 21. Once the mesh 12 is fixed, thread 18 is pulled to remove flexible rod 17 from the mesh 12. Flexible rod 17 with disengagement thread 18 is also depicted in FIG. 2C.

FIG. 2A demonstrates a side perspective view of the mesh 12 along the longitudinal axis and FIG. 2B demonstrates the side view of the mesh 12 alongside the short axis of the mesh 12.

Figure 3:
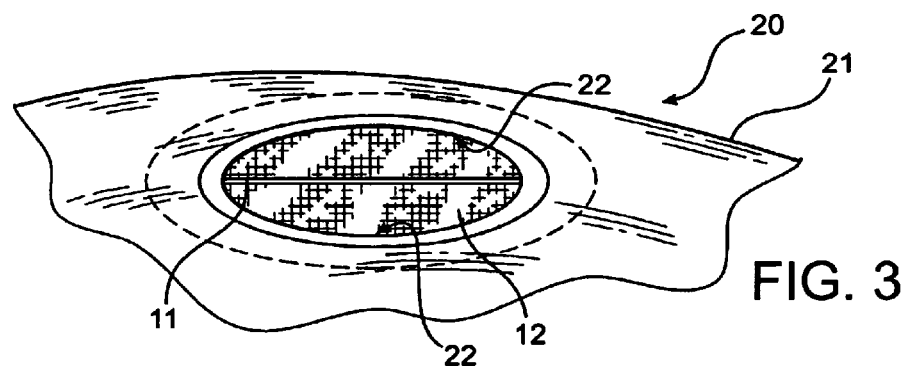
FIG. 3 is a schematic view of the improved mesh inside the abdomen spread on the abdominal wall surface.

FIG. 3 demonstrates the mesh 12 in place inside the abdomen 20 through the hernia defect edges 22 at the depth of the abdominal wall layers 21 and the fixation fin 11 projecting outwardly from the main mesh 12 before approximation of the hernia defect edges 22.

Figure 4:
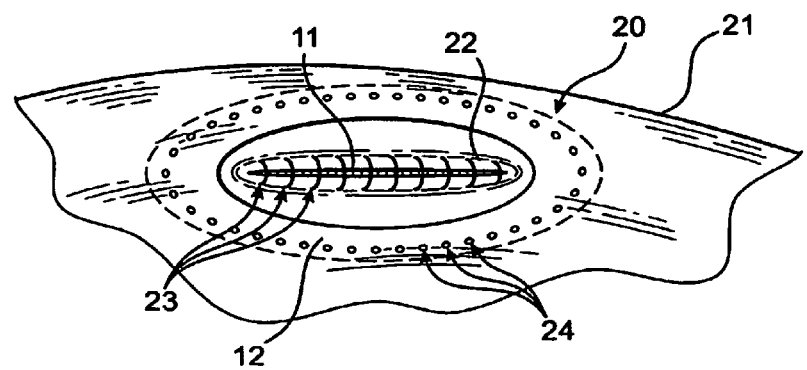
FIG. 4 is a schematic view of the mesh fixed on the posterior surface of the abdominal wall.

FIG. 4 demonstrates the closure of the hernia defect edges 22 with incorporation of the mesh 12 fixation fin 11 with a surgical suture 23 and the mesh 12 fixed inside the abdomen 20 with the appropriate staples 24. The fixation staples 24 are applied laparoscopically with a fixation device on the posterior surface of the abdominal wall 21.

Figure 5:
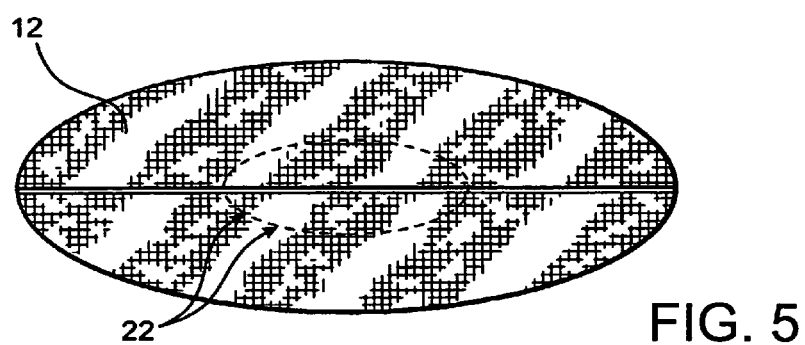
FIG. 5 is a schematic view of the mesh from inside the abdomen viewed laparoscopically.

FIG. 5 demonstrates the mesh 12 viewed from inside the abdomen 20 with the defect location depicted and the central stiff ridge 13 of the mesh 12, which maintains the mesh 12 in the expanded position.

Figure 6:
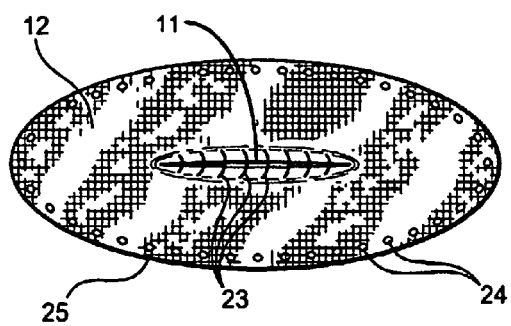
FIG. 6 is a schematic view of the mesh fixed on the posterior surface of the anterior abdominal wall viewed from inside the abdomen.

FIG. 6 demonstrates the mesh 12 viewed from inside the abdomen 20 with the abdominal hernia defect 30 closed and the periphery of the mesh 25 fixed with the appropriate fixation staples 24.

Figure 7:
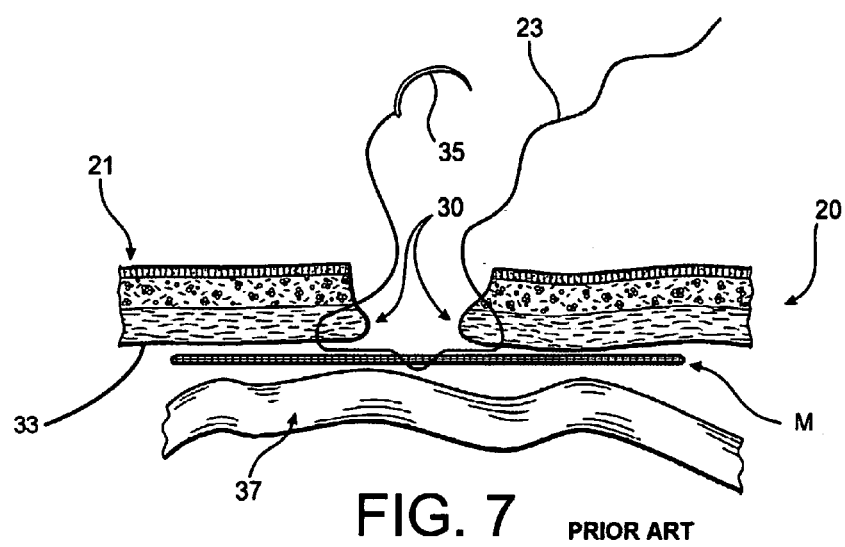
FIG. 7 is a side schematic view of a prior art mesh arranged for suturing in the abdomen to effect a hernia repair.

FIG. 7 is a cross section of the abdomen 20 at the site of an incisional/ventral hernia demonstrating the hernia defect 30 of the abdominal wall 21 with a plurality of layers, with a prior art mesh M spread over the intestine 37, on the peritoneal surface 33.

By using a needle 35, a suture 23 is passed through the edges of the defect 22, and the center of the mesh M.

Figure 7A:
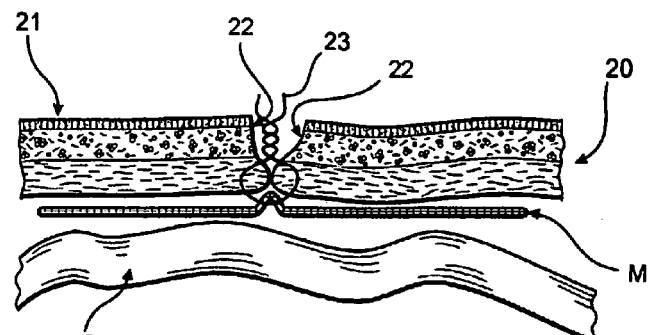
FIG. 7A shows schematically the suture of FIG. 7 tied approximating the hernia defect and incorporating the center of the mesh to close the edges of the hernia defect.

FIG. 7a demonstrates the same cross section of the abdomen 20 with the suture 23 tied, the edges of the hernia defect closed and the center of the mesh M fixed onto the closed hernia defect edges 22 by the same suture 23. The center of the mesh M is wrinkled as a result of the pull of the tied suture 23. This is a problem with the prior art.

Figure 8:
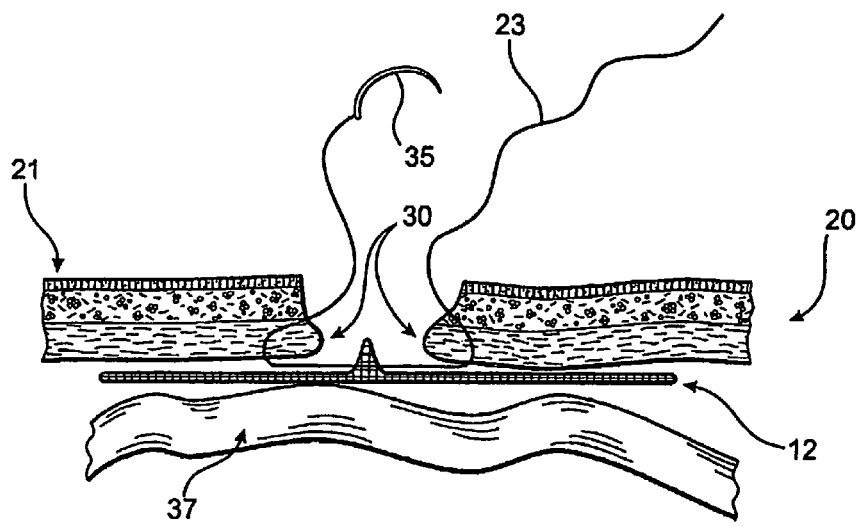
FIG. 8 shows schematically a side view of the hernia repair with suturing; and, FIG. 8A shows schematically the suture of FIG. 8 tied approximating the hernia defect and incorporating the fixation fin.
Figure 8A:
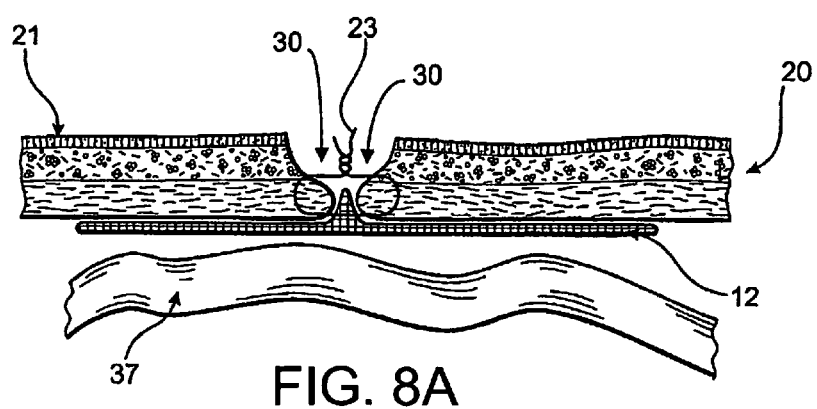
Figure 9A:
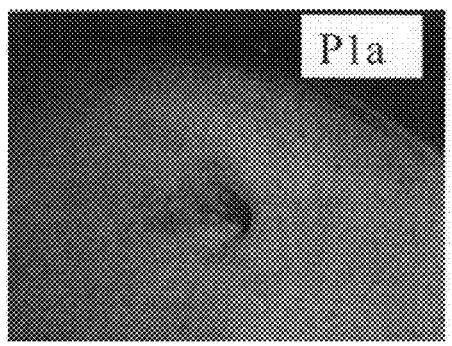
Figure 9B:
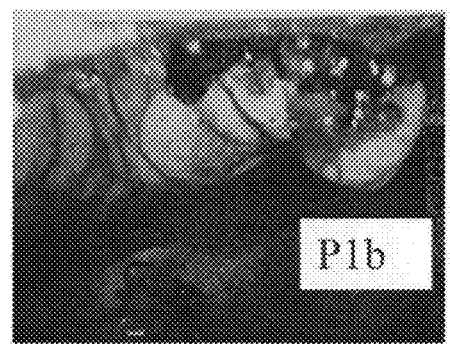
Figure 9C:
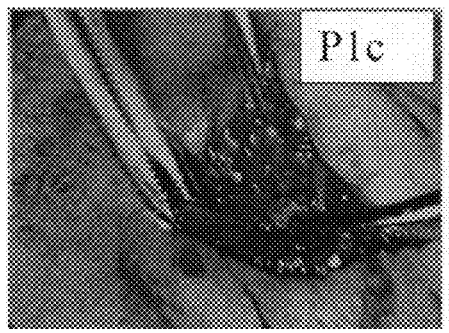
Figure 9D:
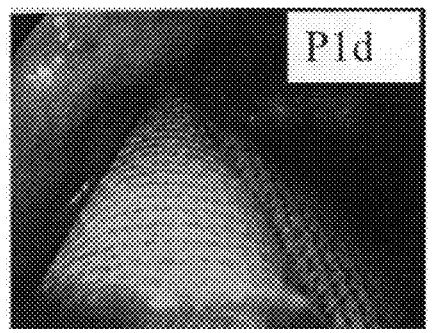
Figure 10A:
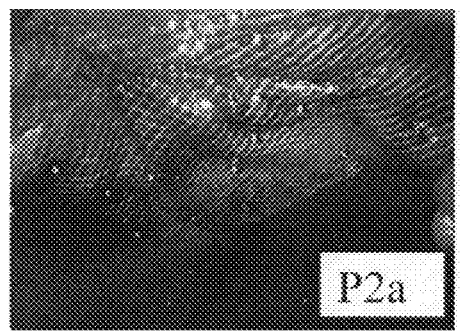
Figure 10B:
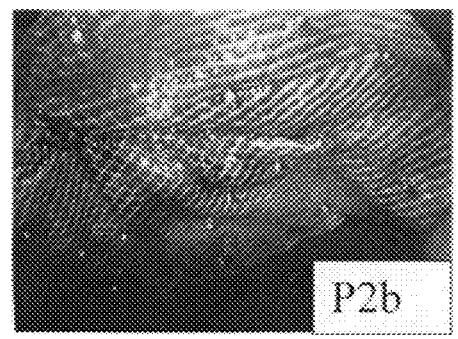
Figure 10C:
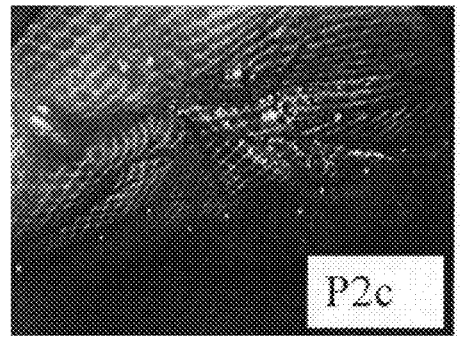
Figure 10D:
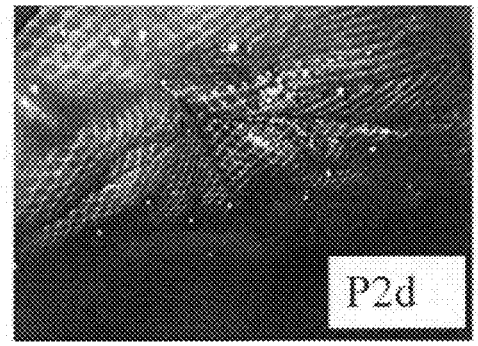

FIG. 8 is a cross-section of the abdomen 20 as in FIG. 7 with the only difference that the mesh 12 has the fixation fin 11 of the new and improved mesh 12. The suture 23 is passed through the fixation fin 11, instead of the center of the main body of the mesh 12. Potential problems and injury are thus prevented.

While the invention has been explained by a detailed description of certain specific embodiments, it is understood that various modifications and substitutions can be made in any of them within the scope of the appended claims that are intended also to include equivalents of such embodiments.

What is claimed is:

1. A surgical mesh for laparoscopically repairing a hernia defect in a patient's abdominal wall, the mesh comprising:
    a sheet of a mesh material suitable for attaching to the peritoneal surface of the patient's abdominal wall and having an extent greater than the size of a hernia defect to be repaired;
    a stiffening ridge extending along a surface of the sheet for assisting laparoscopic placement of the sheet after the sheet has been inserted inside the patient's abdomen; and
    a fixation fin having a proximal edge attached to the stiffening ridge and extending along the sheet for a distance less than the extent thereof and a distal edge raised above the surface of the sheet a sufficient distance to permit attachment of the fixation fin to an edge of a hernia defect when the sheet is in place inside the patient's abdomen with the sheet surface facing the peritoneal surface of the patient's abdominal wall,
    wherein the fixation fin is located on the sheet with opposing ends of the fixation fin spaced a predetermined distance from corresponding edges of the sheet for providing an excess area surrounding the proximal edge of the fixation fin in all directions a sufficient distance to allow attachment of the sheet to the peritoneal surface of the patient's abdominal wall at any desired location on the sheet when the fixation fin is in place for attachment to the edge of the hernia defect, and the stiffening ridge extends along the sheet in two directions beyond the proximal edge of the fixation fin a sufficient distance to assist in laparoscopic placement of the sheet after the sheet has been inserted inside the patient's abdomen.

2. A surgical mesh as in claim 1, wherein the stiffening ridge and the fixation fin are a single structure having a straight edge attached to said surface of the sheet and the distal edge of the fixation fin is raised above said surface a greater distance than the stiffening ridge.

3. A surgical mesh as in claim 2, wherein the straight edge bisects said surface of the sheet and the stiffening ridge extends to the edges of the sheet.

4. A surgical mesh as in claim 3, wherein the sheet, the stiffening ridge, and the fixation fin are a one-piece structure.

5. A surgical mesh as in claim 2, wherein the stiffening ridge is straight and extends to the edges of the sheet.

6. A surgical mesh as in claim 5, wherein the sheet is longer in the direction of the stiffening ridge than in a width direction transverse thereto.

7. A surgical mesh as in claim 1, wherein the fixation tin is longer at the proximal edge than at the distal edge.

8. A surgical mesh as in claim 1, wherein the sheet is continuous.

9. A surgical mesh as in claim 5, wherein the sheet, the stiffening ridge, and the fixation fin are a one-piece structure.

10. A surgical mesh for laparoscopically repairing a hernia defect in a patient's abdominal wall, the mesh comprising:
   a sheet of a mesh material suitable for attaching to the peritoneal surface of the patient's abdominal wall and having an extent greater than the size of a hernia defect to be repaired;
   a fixation tin having a proximal edge attached to a surface of the sheet and extending along the sheet for a distance less than the extent thereof and a distal edge raised above the surface of the sheet a sufficient distance to permit attachment of the fixation fin to an edge of a hernia defect when the sheet is in place inside the patient's abdomen with the sheet surface facing the peritoneal surface of the abdominal wall; and a straight stiffening ridge for assisting laparoscopic placement of the sheet after the sheet has been inserted inside the patient's abdomen,
   wherein the fixation fin is located on the sheet so that no location on the peripheral edge of the sheet is closer than about four cm to the proximal edge of the fixation fin and the fixation fin proximal edge is attached to the stiffening ridge with the distal edge of the fixation fin raised above the surface a greater distance than the stiffening ridge and the stiffening ridge extends along the sheet in two directions beyond the proximal edge of the fixation fin.

11. A surgical mesh as in claim 10, wherein the fixation fin is longer at the proximal edge than at the distal edge.

12. A surgical mesh for laparoscopically repairing a hernia defect in a patient's abdominal wall, the mesh comprising:
   a continuous sheet comprising a mesh material having an extent greater than the size of a hernia defect to be repaired, the mesh material being suitable for attaching to the peritoneal surface of the patient's abdominal wall;
   a stiffing ridge extending along a surface of the sheet; and
   a fixation fin having a proximal edge attached to the stiffening ridge and extending along the sheet for a distance less than the extent thereof and a distal edge raised above the surface of the sheet a sufficient distance to permit attachment of the fixation fin to an edge of a hernia defect when the sheet is in place inside the patient's abdomen with the sheet surface facing the peritoneal surface of the abdominal wall,
   wherein the fixation fin is located on the sheet with opposing ends of the fixation fin spaced a predetermined distance from corresponding edges of the sheet for providing an excess area surrounding the proximal edge of the fixation fin in all directions a sufficient distance to allow attachment of the sheet to the peritoneal surface of the patient's abdominal wall at any desired location on the sheet when the fixation fin is in place for attachment to the edge of the hernia defect, and the stiffening ridge extends in two directions beyond the proximal edge of the fixation fin.

13. A surgical mesh as in claim 12, further comprising a straight stiffening ridge bisecting a surface of the sheet and extending to the edges thereof for assisting laparoscopic placement of the sheet after the sheet has been inserted inside the patient's abdomen, wherein the fixation fin proximal edge is attached to the stiffening ridge and the stiffening ridge and the fixation fin are a single structure with the distal edge of the fixation fin raised above said surface a greater distance than the stiffening ridge.

14. A surgical mesh as in claim 13, wherein the sheet is longer in the direction of the stiffening ridge than in a width direction transverse thereto.

15. A surgical mesh as in claim 13, wherein the sheet, the stiffening ridge, and the fixation fin are a one-piece structure.

16. A surgical mesh as in claim 12, wherein the fixation fin is longer at the proximal edge than at the distal edge.

17. A surgical mesh as in claim 12, wherein the excess area is provided by spacing the peripheral edge of the sheet at least about four cm from the proximal edge of the fixation fin in all directions.

* * * * *